United States Patent [19]

Nagano et al.

[11] Patent Number: 5,051,509
[45] Date of Patent: Sep. 24, 1991

[54] NOVEL QUINOLONECARBOXYLIC ACID DERIVATIVES

[75] Inventors: Hiroyuki Nagano, Saitama; Takeshi Yokota, Chiba; Yasuyuki Katoh, Shizuoka, all of Japan

[73] Assignee: Chugai Seiyaku Kabushiki Kaisha, Tokyo, Japan

[21] Appl. No.: 354,962

[22] Filed: May 22, 1989

[30] Foreign Application Priority Data

Dec. 8, 1988 [JP] Japan .................. 63-310418

[51] Int. Cl.$^5$ .................. C07D 401/04; A61K 31/47
[52] U.S. Cl. .................. 546/156
[58] Field of Search ............... 546/156; 514/312

[56] References Cited

U.S. PATENT DOCUMENTS

| | | | |
|---|---|---|---|
| 4,771,055 | 9/1988 | Domagala et al. | 546/156 |
| 4,777,175 | 10/1988 | Culbertson et al. | 546/156 |
| 4,851,418 | 7/1989 | Sanchez | 546/156 |
| 4,997,943 | 3/1991 | Iwata et al. | 544/363 |

FOREIGN PATENT DOCUMENTS

| | | |
|---|---|---|
| 0230295 | 7/1987 | European Pat. Off. . |
| 241206 | 10/1987 | European Pat. Off. . |
| 469 | 1/1987 | Japan .................. 546/156 |

*Primary Examiner*—Mukund J. Shah
*Assistant Examiner*—E. Bernhardt
*Attorney, Agent, or Firm*—Browdy and Neimark

[57] ABSTRACT

Novel compounds of the present invention are represented by the general formula (1)

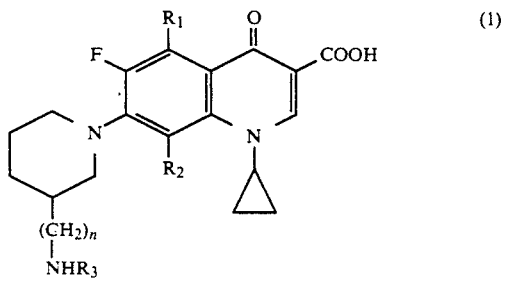

wherein $R_1$ is hydrogen atom or amino, $R_2$ is fluorine atom or methoxy, $R_3$ is hydrogen atom or a lower alkyl having 1 to 3 carbon atoms, and n is 0 or 1. The compounds of the general formula (1) exhibit higher antibacterial activity with fewer side-effects than known quinolone antibiotics such as ofloxacin and norfloxacin. Further, the compounds having the general formula (1) have reduced phototoxicity which normally accompanies 6,8-defluoroquinoline antibiotics.

2 Claims, No Drawings

NOVEL QUINOLONECARBOXYLIC ACID DERIVATIVES

FIELD OF THE INVENTION

The present invention relates to novel quinolonecarboxylic acid derivatives that exhibit strong antibacterial activity and are useful as medicines.

BACKGROUND OF THE INVENTION

A number of quinolone antibiotics are known, including commercially available ones, but they involve certain problems such as the fact that these compounds must be used with utmost caution because many of them show side-effects in the central nervous system. Recently, much attention has been paid to the antibacterial activity of quinoline derivatives that have a fluorine substituent at both 6- and 8-position, or a fluorine substituent at 6-position and a lower alkoxy substituent at 8-position (U.S. Pat. No. 4,556,658, European Patent No. 106,489, European Patent Laid Open No. 230,295, European Patent Laid Open No. 241,206). However, they are not always satisfactory antibiotics, since many of them have phototoxicity along with the side-effects mentioned above.

SUMMARY OF THE INVENTION

The present inventors zealously investigated ways of eliminating the drawbacks of quinolone antibiotics and found that compounds of the general formula (1) shown below which have at 7-position a piperidin-1-yl group whose 3-position is substituted by an amino, lower alkyl or aminomethyl group, for example, 3-amino-piperidin-1-yl group, exhibit higher antibacterial activity with fewer side-effects than known quinolone antibiotics such as ofloxacin and norfloxacin. Further, the compounds of the present invention having the general formula (1) have reduced phototoxicity which normally accompanies 6,8-difluoroquinoline antibiotics.

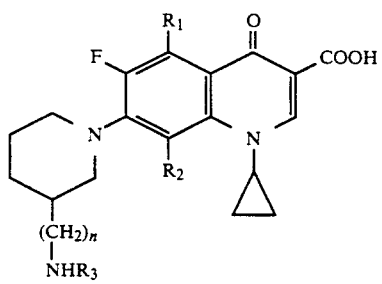

(1)

(wherein $R_1$ is hydrogen atom or amino, $R_2$ is fluorine atom or methoxy, $R_3$ is hydrogen atom or a lower alkyl having 1 to 3 carbon atoms, and n is 0 or 1).

The quinolone derivatives of this invention having the general formula (1) are novel compounds. Those which have a fluorine atom at 8-position can be provided by the reaction of 3-acetamidopiperidines with known starting materials, for example, 1-cyclopropyl-6,7,8-trifluoro-1,4-dihydro-4-oxoquinoline-3-carboxylic acid, 5-amino-1-cyclopropyl-6,7,8-trifluoro-1,4-dihydro-4-oxoquinoline-3-carboxylic acid or a lower alkyl ester thereof followed by hydrolysis. Compounds of the invention having the general formula (1) where a methoxy group exists at 8-position may be provided by the reaction of the compound obtained from the foregoing step with sodium methoxide. While there exist two optical isomers of each compound of the invention having the general formula (1), both of them can be utilized as compounds of the invention. In the case of synthesis of an optical active compound, for instance, starting with 3-aminopiperidine that has been prepared from optically active ornithine, the synthesis may be performed in a manner similar to that described above.

DETAILED DESCRIPTION OF THE INVENTION

Preferable examples of the compound of the invention having the general formula (1) include the following: 7-(3-aminopiperidin-1-yl)-1-cyclopropyl-6,8-difluoro-1,4-dihydro-4-oxoquinoline-3-carboxylic acid, (S)-7-(3-amino-1-piperidin-1-yl)-1-cyclopropyl-6,8-difluoro-1,4-dihydro-4-oxoquinoline-3-carboxylic acid, (R)-7-(3-aminopiperidin-1-yl)-1-cyclopropyl-6,8-difluoro-1,4-dihydro-4-oxoquinoline-3-carboxylic acid, 7-(3-aminopiperidin-1-yl)-1-cyclopropyl-6-fluoro-1,4-dihydro-8-methoxy-4-oxoquinoline-3-carboxylic acid, 5-amino-7-(3-aminopiperidin-1-yl)-1-cyclopropyl-6,8-difluoro-1,4-dihydro-4-oxoquinoline-3-carboxylic acid, 7-(3-aminomethylpiperidin-1-yl)-1-cyclopropyl-6,8-difluoro-1,4-dihydro-4-oxoquinoline-3-carboxylic acid, 1-cyclopropyl-6-fluoro-1,4-dihydro-8-methoxy-7-(3-methylaminopiperidin-1-yl)-4-oxoquinoline-3-carboxylic acid, 5-amino-1-cyclopropyl-6-fluoro-1,4-dihydro-8-methoxy-7-(3-methylaminopiperidin-1-yl)-4-oxoquinoline-3-carboxylic acid, and 7-(3-aminomethylpiperidin-1-yl)-1-cyclopropyl-6-fluoro-1,4-dihydro-8-methoxy-4-oxoquinoline-3-carboxylic acid.

The compounds of the invention form salts with acids. Examples of pharmaceutically acceptable acids include inorganic acids such as hydrochloric acid, sulfuric acid and nitric acid and organic acids such as oxalic acid, fumaric acid, and p-toluenesulfonic acid. The antibacterial activity of a typical compound of the invention (the compound which will be described in Example 1) was compared with that of known quinolone antibiotics such as ofloxacin and norfloxacin by measuring MIC values. The results are shown in Table 1. The MIC values were measured by means of a conventional method.

TABLE 1

| | Sample Compound (μg/ml) | | | |
| --- | --- | --- | --- | --- |
| Organisms | Compound Ex. 1 | nalidixic acid[*1] | ofloxacin[*2] | norfloxacin[*3] |
| Staphylococcus aureus FDA 209P JC-1 | 0.012 | 12.5 | 0.10 | 0.05 |
| Escherichia coli NIHJ JC-2 | 0.024 | 6.25 | 0.05 | 0.05 |
| Klebsiella pneumoniae No. 42 | 0.024 | 1.56 | 0.05 | 0.05 |
| Proteus mirabilis JY10 | 0.012 | 0.78 | 0.012 | 0.012 |
| Serrata marcescens No. 16-2 | 0.20 | 0.78 | 0.78 | 0.39 |
| Pseudomonas aeruginosa AK 109 | 0.39 | 100 | 0.39 | 0.20 |

TABLE 1-continued

| Organisms | Sample Compound (μg/ml) | | | |
|---|---|---|---|---|
| | Compound Ex. 1 | nalidixic acid*1 | ofloxacin*2 | norfloxacin*3 |
| *Pseudomonas cepacia* 23 | 12.5 | 50 | 12.5 | 25 |

*1

*2

*3

As indicated in Table 1, the compound of this invention possesses higher antibacterial activity than the known quinolone antibiotics. The characteristic feature of the compounds of the invention is that the antibacterial activity thereof is particularly high against Gram-positive bacteria.

The phototoxicity of a typical compound of the invention was compared with that of the known 6,8-difluoroquinoline antibiotics shown below as reference compounds and the results are summarized in Table 2. The compound which will be described in Example 1 was used as being typical of this invention.

reference compound A:

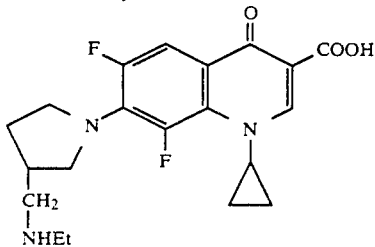

reference compound B:

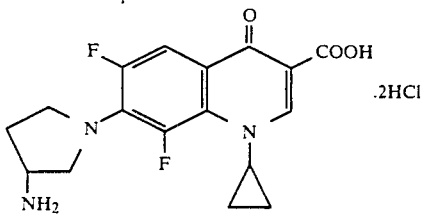

a compound of this invention:

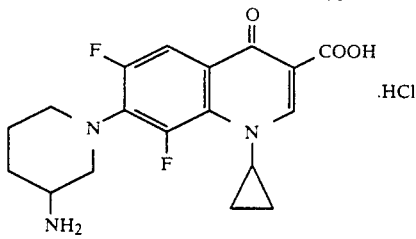

TABLE 2

Effect of difluoro-quinolones on increased wet-weight of murine tails following UVA exposure

| Dose$^a$ (mg/kg) | Wet weight of tail tissue (%)$^b$ | | |
|---|---|---|---|
| | Compound Ex. 1 | Compound A | Compound B |
| water | 63.6 ± 0.49 | 62.8 ± 0.4 | 62.0 ± 0.49 |
| 12.5 | 62.5 ± 0.82 NS$^c$ | 63.6 ± 1.9 NS | 64.1 ± 0.29 < 0.005 |
| 50 | 64.5 ± 1.5 NS | 70.2 ± 1.5 < 0.001 | 69.0 ± 0.57 < 0.001 |

Experimental Method
$^a$Male ddY/Crj mice, 5 week-old, were administered orally the indicated doses of difluoro-quinolones and then immobolized completely in plastic tubes with orifices for ventilation and tails. Immediately afterwards, the mouse tails were exposed to 4.5–5.5 hours radiation of long-wave ultraviolet light (UVA) emitted from two black-light tubes (TOSHIBA FL 40S BLB) kept 11 cm above the tails. The intensity of radiation was 1.30–1.80 mW/cm$^2$.
$^b$The relative water content (wet weight) was calculated by weighing before and immediately after drying at 110° C. for 3 hours.
$^c$The results were analysed statistically by the Student's t test. NS = not significant.

As indicated in Table 2, the compound of this invention exhibits lower phototoxicity than the known quinolone antibiotics.

The following examples illustrate the inventors' methods for preparing the compounds of this invention.

EXAMPLE 1

(a) A mixture of ethyl 1-cyclopropyl-6,7,8-trifluoro-1,4-dihydro-4-oxoquinoline-3-carboxylate (933 mg), 3-acetamidopiperidine (710 mg), triethylamine (400 mg)

and dimethylsulfoxide (10 ml) was heated at 100° C. for 2 hours with stirring. Thereafter the mixture was cooled down and ice water was added thereto. The resulting mixture was extracted with chloroform and the chloroform layer was washed with water three times before being dried over anhydrous sodium sulfate. Removal of the solvent in vacuum followed by purification by silica gel column chromatography (chloroform-ethanol) gave ethyl 7-(3-acetamidopiperidin-1-yl)-1-cyclopropyl-6,8-difluoro-1,4-dihydro-4-oxoquinoline-3-carboxylate (930 mg). Recrystallization from ethanol-ether afforded a colorless crystalline substance (m.p. 217°–218° C.).

(b) Ethyl 7-(3-acetamidopiperidin-1-yl)-1-cyclopropyl-6,8-difluoro-1,4-dihydro-4-oxoquinoline-3-carboxylate obtained from the foregoing step (a) (433 mg) was dissolved in 6N hydrochloric acid (5 ml) and heated at 100° C. for 2.5 hours with stirring. After the removal of the solvent in vacuum, methanol was added to the residue and the insoluble materials were filtered off. Removal of the solvent followed by purification by silica gel column chromatography (chloroform-methanol) gave hydrochloride of 7-(3-aminopiperidin-1-yl)-1-cyclopropyl-6,8-difluoro-1,4-dihydro-4-oxoquinoline-3-carboxylic acid (colorless, crystalline-powder), m.p.: color change at about 272° C.; decomposition at about 280° C.

IR (KBr) $\nu$ cm$^{-1}$: 1735, 3450
MS m/e: 363 (M+), 362

EXAMPLE 2

To a solution of 7-(3-aminopiperidin-1-yl)-1-cyclopropyl-6,8-difluoro-1,4-dihydro-4-oxoquinoline-3-carboxylic acid dihydrate (7.98 g) obtained as described in Example 1 in 400 ml of methanol-water (3:1) was added a solution of p-toluenesulfonic acid monohydrate (4.0 g) in 100 ml of water. The reaction mixture was concentrated in vacuum to half of the initial volume and cooled down. Filtration of the precipitated crystalline gave p-toluenesulfonic acid salt of 7-(3-aminopiperidin-1-yl)-1-cyclopropyl-6,8-difluoro-1,4-dihydro-4-oxoquinoline-3-carboxylic acid (9.7 g) as colorless needles (m.p. about 300° C.).

EXAMPLE 3

A mixture of 1-cyclopropyl-6,7,8-trifluoro-1,4-dihydro-4-oxoquinoline-3-carboxylic acid (566 mg), 3-acetamidopiperidine (300 mg), triethylamine (220 mg) and dimethylsulfoxide (10 ml) was heated at 100° C. for 2 hours with stirring. Thereafter the mixture was cooled to room temperature and ice water was added thereto. The precipitated crystalline was filtered off and washed with methanol-ether to give 7-(3-acetamidopiperidin-1-yl)-1-cyclopropyl-6,8-difluoro-1,4-dihydro-4-oxoquinoline-3-carboxylic acid (540 mg) (m.p. 280°–282° C., recrystallized from methanol). The product (405 mg) obtained in the above manner was suspended in 6N hydrochloric acid (5 ml) and heated at 100° C. for 2.5 hours with stirring. The reaction mixture was further processed in a similar manner to step (b) of Example 1 to afford hydrochloride of 7-(3-aminopiperidinly-1)-1-cyclopropyl-6,8-difluoro-1,4-dihydro-4-oxoquinoline-3-carboxylic acid. The physical properties of this product were identical with those of the compound provided in Example 1.

EXAMPLE 4

(a) To a solution of L-ornithine monohydrate (25 g) in methanol (200 ml) was added dropwise thionyl chloride (32.6 ml) under cooling and stirring and the reaction mixture was refluxed. After 6 hours the solvent was removed in vacuum and the residue was then treated with isopropyl ether (300 ml) and the precipitated solid filtered off to give L-ornithine methyl ester dihydrochloride (33.09 g) as a colorless powder (hygroscopic).

NMR (D$_2$O) $\delta$:1.80–2.60 (4H, m), 3.35 (2H distorted t, J=8 Hz), 4.13 (3H, s), 4.51 (1H, t, J=6 Hz)

(b) A solution of L-ornithine methyl ester dihydrochloride (62.0 g) obtained as described in the step (a) above in cold water (300 ml) was passed through a column packed with Amberlite IRA-40 (OH$^-$) ion-exchange resin and ninhydrine positive fractions were collected. Removal of the solvent gave (S)-3-aminopiperidone (44.5 g) as a colorless oil (hygroscopic).

IR (KBr) $\nu_{max}$ cm$^{-1}$: 1660

(c) To a suspension of lithium aluminum hydride (22.8 g) in tetrahydrofuran (1000 ml) was added a suspension of (S)-3-aminopiperidone (20.0 g) obtained from the step (b) above in tetrahydrofuran (300 ml) under ice-cooling and stirring. The reaction mixture was refluxed for 6 hours then the excess lithium aluminum hydride was carefully quenched with aqueous 10% sodium hydroxide under ice-cooling and stirring. The precipitated inorganic materials were filtered off and the filtrate was concentrated in vacuum. The oily residue was distilled and a fraction having bp$_{760}$ 130°–160° C. was collected to obtain (S)-3-aminopiperidine (3.0 g) as colorless oil (solidified during distillation, hygroscopic).

(d) A suspension of (S)-3-aminopiperidine (4.0 g) obtained as described in the step (c) above 1-cyclopropyl-6,7,8-trifluoro-1,4-dihydro-4-oxoquinoline-3-carboxylic acid (11.4 g) and triethylamine (8.4 g) in acetonitrile (250 ml) was refluxed for 3 hours with stirring. Then the mixture was cooled down and filtration of the precipitated powder followed by treatment with a mixture of ethanol (550 ml) and water (250 ml) gave (S)-7-(3-aminopiperidin-1-yl)-1-cyclopropyl-6,8-difluoro-1,4-dihydro-4-oxoquinoline-3-carboxylic acid (11.6 g) as colorless needles. m.p. 247.8° C. (decomposition).

$[\alpha]_D^{20}$=+19.9° (c=1.002, 0.1N NaOH) IR (KBr) $\nu_{max}$cm$^{-1}$: 1675, 1660, 1640 NMR (CDCl$_3$) $\delta$:1.10–1.40 (4H, m), 2.90–3.60 (9H, m), 3.95–4.05 (1H, m), 7.83 (1H, dd, J=12 Hz, J=2 Hz), 9.78 (1H, s).

EXAMPLE 5

(R)-3-aminopiperidine obtained from D-ornithine monohydrochloride as the starting material in a similar manner to that described in Example 4(a)-(c) was reacted with 1-cyclopropyl-6,7,8-trifluoro-1,4-dihydro-4-oxoquinoline-3-carboxylic acid in accordance with the procedure described in Example 4(d) to afford (R)-7-(3-aminopiperidin-1-yl)-1-cyclopropyl-6,8-difluoro-1,4-dihydro-4-oxoquinoline-3-carboxylic acid. m.p. 252.3° C. (decomposition).

$[\alpha]_D^{20}$=−15.5° (c=0.991, 0.1N NaOH) IR (KBr) $\nu_{max}$cm$^{-1}$: 1665, 1650, 1630 NMR (CDCl$_3$) $\delta$:1.10–1.40 (4H, m), 2.90–3.60 (9H, m), 3.90–4.10 (1H, m), 7.86 (1H, dd, J=12 Hz, J=2 Hz), 8.76 (1H, s).

EXAMPLE 6

(a) A mixture of 7-(3-acetamidopiperidin-1-yl)-1-cyclopropyl-6,8-difluoro-1,4-dihydro-4-oxoquinoline-3-carboxylic acid (4.05 g), sodium methoxide (2.16 g) and N,N-dimethylformamide (120 ml) was stirred for 2 hours at 100°–140° C. The reaction mixture was concentrated in vacuum and water was added to the residue. The mixture was neutralized with 1N hydrochloric acid and the neutralized mixture was then concentrated in vacuum. Purification of the concentrated mixture by silica gel column chromatography (chloroform-methanol) gave 7-(3-acetamidopiperidin-1-yl)-1-cyclopropyl-6-fluoro-1,4-dihydro-8-methoxy-4-oxoquinoline-3-carboxylic acid. m.p. 248°–250° C.

(b) 7-(3-Acetamidopiperidin-1-yl)-1-cyclopropyl-6-fluoro-1,4-dihydro-8-methoxy-4-oxoquinoline-3-carboxylic acid (1.25 g) obtained from the foregoing step (a) was suspended in 6N hydrochloric acid (30 ml) and ethanol (5 ml) and heated at 100° C. for 3 hours. Then the reaction mixture was concentrated in vacuum and the residue was purified by silica gel column chromatography (chloroform:methanol:ammonium hydroxide=100:30:5) to afford 7-(3-aminopiperidin-1-yl)-1-cyclopropyl-6-fluoro-1,4-dihydro-8-methoxy-4-oxoquinoline-3-carboxylic acid. m.p. 176°–177° C.

EXAMPLE 7

A mixture of 7-(3-aminopiperidin-1-yl)-1-cyclopropyl-6,8-difluoro-1,4-dihydro-4-oxoquinoline-3-carboxylic acid (1.21 g) obtained as described in Example 1(b), sodium methoxide (1.2 g) and dimethylsulfoxide (40 ml) was stirred for 2 hours at 120°–140° C. The reaction mixture was concentrated in vacuum and water was added to the residue. Neutralization of the mixture with 1N hydrochloric acid followed by evaporation of the solvent and purification by silica gel column chromatography (chloroform:methanol:ammonium hydroxide=100:30:5) gave 7-(3-aminopiperidin-1-yl)-1-cyclopropyl-6-fluoro-1,4-dihydro-8-methoxy-4-oxoquinoline-3-carboxylic acid. The physical properties of this product were identical with those of the compound obtained in Example 6.

EXAMPLE 8

To a suspension of 7-(3-aminopiperidin-1-yl)-1-cyclopropyl-6-fluoro-1,4-dihydro-8-methoxy-4-oxoquinoline-3-carboxylic acid obtained as described in Example 6 or 7 in a mixture of chloroform and methanol (1:1) was added dropwise methanolic hydrochloric acid and the mixture was worked up in a conventional manner to give hydrochloride of 7-(3-aminopiperidin-1-yl)-1-cyclopropyl-6-fluoro-1,4-dihydro-8-methoxy-4-oxoquinoline-3-carboxylic acid. m.p. 188°–190° C. (decomposition).

EXAMPLE 9

A suspension of 5-amino-1-cyclopropyl-6,7,8-trifluoro-1,4-dihydro-4-oxoquinoline-3-carboxylic acid (1.3 g), 3-aminopiperidine hydrochloride (0.905 g), triethylamine (3.0 g) in acetonitrile (40 ml) was refluxed for 5 hours and the reaction mixture was then cooled to room temperature. Removal of the solvent followed by purification by silica gel column chromatography (chloroform:methanol:ammonium hydroxide=15:5:1) gave a yellow crystalline substance [MS m/e: 378 (M+)]. The crystalline substance thus obtained was suspended in isopropanol and the suspension was adjusted to pH about 1-2 with 10% aqueous hydrochloric acid. Filtration of the precipitated crystals followed by recrystallization from ethanol afforded hydro-chloride of 5-amino-7-(3-aminopiperidin-1-yl)-1-cyclopropyl-6,8-difluoro-1,4-dihydro-4-oxoquinoline-3-carboxylic acid (0.6 g). m.p. 265° C. (decomposition).

EXAMPLE 10

A suspension of 5-amino-1-cyclopropyl-6,7-difluoro-1,4-dihydro-8-methoxy-4-oxoquinoline-3-carboxylic acid (1.039 g), 3-methylaminopiperidine hydrochloride (1.5 g) and triethylamine (2.5 g) in acetonitrile (30 ml) and N,N-dimethylformamide (10 ml) was refluxed overnight. Concentration of the reaction mixture followed by purification by silica gel column chromatography (chloroform:methanol:ammonium hydroxide=15:5:1) gave a yellow crystalline substance [MS m/e: 404 (M+)]. The crystalline substance thus obtained was recrystallized from ethanol to afford 5-amino-7-(3-methylaminopiperidin-1-yl)-1-cyclopropyl-6-fluoro-1,4-dihydro-8-methoxy-4-oxoquinoline-3-carboxylic acid (400 mg) as yellow needles. m.p. 265°–275° C. (decomposition).

EXAMPLE 11

A suspension of 1-cyclopropyl-6,7-difluoro-1,4-dihydro-8-methoxy-4-oxoquinoline-3-carboxylic acid (1.48 g), 3-aminomethylpiperidine (1.14 g) and triethylamine (1.5 g) in acetonitrile (20 ml) and N,N-dimethylformamide (10 ml) was refluxed overnight. Concentration of the reaction mixture followed by purification by silica gel column chromatography (chloroform:methanol:ammonium hydroxide=15:5:1) gave 7-(3-aminomethylpiperidin-1-yl)-1-cyclopropyl-6-fluoro-1,4-dihydro-8-methoxy-4-oxoquinoline-3-carboxylic acid, which was recrystallized from isopropanol-water to afford yellow prisms. m.p. 192°–193° C.

MS m/e: 389 (M+)

EXAMPLE 12

A mixture of 1-cyclopropyl-6,7,8-trifluoro-1,4-dihydro-4-oxoquinoline-3-carboxylic acid (2.83 g), 3-acetamidomethylpiperidine (1.87 g) and triethylamine (1.5 g) in acetonitrile (60 ml) was refluxed with stirring for 6 hours. The precipitate was filtered to give 7-(3-acetamidomethylpiperidin-1-yl)-1-cyclopropyl-6,8-difluoro-1,4-dihydro-4-oxoquinoline-3-carboxylic acid (3.5 g). The product (3.0 g) was suspended in 6N hydrochloric acid (50 ml) and heated at 100° C. with stirring for 5 hours. The reaction mixture was concentrated in vacuum, and the crude material was dissolved in 20 ml of aqueous ammonium hydroxide under ice-cooling. Removal of the solvent followed by purification by silica gel column chromatography (chloroform:methanol:ammonium hydroxide=15:5:1) gave 7-(3-aminomethylpiperidin-1-yl)-1-cyclopropyl-6,8-difluoro-1,4-dihydro-4-oxoquinoline-3-carboxylic acid (1.6 g), which was recrystallized from methanol-water to afford colorless prisms. m.p. 242°–243° C.

MS m/e: 377 (M+)

EXAMPLE 13

A mixture of 1-cyclopropyl-6,7-difluoro-1,4-dihydro-8-methoxy-4-oxoquinoline-3-carboxylic acid (2.95 g), 3-methylaminopiperidine dihydrochloride (6.69 g) and triethylamine (10 g) in acetonitrile (50 ml) was refluxed with stirring for 12 hours. The reaction mixture was concentrated in vacuum, and the residue was extracted with chloroform. The extract was washed with a saturated NaCl solution and concentrated in vacuo. The residue was purified by silica gel column chromatography (chloroform:methanol:ammonium hydroxide=15:5:1) to give 1.28 g of 1-cyclopropyl-6-fluoro-1,4-dihydro-8-methoxy-7-(3-methylaminopiperidin-1- yl)-4-oxoquinoline-3-carboxylic acid, which was recrystallized from acetonitrile-water, colorless needles. m.p. 134°–135° C.

What is claimed is:

1. 1-cyclopropyl-6-fluoro-1,4-dihydro-8-methoxy-7-(3-methylaminopiperidin-1-yl)-4-oxoquinoline-3-carboxylic acid.

2. 5-Amino-1-cyclopropyl-6-fluoro-1,4-dihydro-8-methoxy-7-(3-methylaminopiperidin-1-yl)-4-oxoquinoline-3-carboxylic acid.

* * * * *